United States Patent
Dirkes et al.

(10) Patent No.: US 10,973,428 B2
(45) Date of Patent: Apr. 13, 2021

(54) DEVICE AND METHOD FOR MEASURING A PHYSIOLOGICAL CHARACTERISTIC OF A SUBJECT

(71) Applicant: KONINKLIJKE PHILIPS N.V., Eindhoven (NL)

(72) Inventors: Marcel Cornelis Dirkes, The Hague (NL); Rick Bezemer, Amsterdam (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 488 days.

(21) Appl. No.: 15/533,662

(22) PCT Filed: Dec. 10, 2015

(86) PCT No.: PCT/EP2015/079179
§ 371 (c)(1),
(2) Date: Jun. 7, 2017

(87) PCT Pub. No.: WO2016/091984
PCT Pub. Date: Jun. 16, 2016

(65) Prior Publication Data
US 2017/0340228 A1    Nov. 30, 2017

(30) Foreign Application Priority Data

Dec. 12, 2014    (EP) .................................... 14197715

(51) Int. Cl.
*A61B 5/04*    (2006.01)
*A61B 5/0456*    (2006.01)
(Continued)

(52) U.S. Cl.
CPC .......... *A61B 5/0456* (2013.01); *A61B 5/0245* (2013.01); *A61B 5/02125* (2013.01);
(Continued)

(58) Field of Classification Search
CPC ... A61B 5/01; A61B 5/02125; A61B 5/02427; A61B 5/0245; A61B 5/04012;
(Continued)

(56) References Cited

U.S. PATENT DOCUMENTS 9,642,543 B2 *    5/2017    Banerjee ............ A61B 5/02405
2003/0004547 A1    1/2003    Fincke
(Continued)

FOREIGN PATENT DOCUMENTS

DE    19602347    7/1997
EP    1977688    10/2008
(Continued)

OTHER PUBLICATIONS

Karvounis, et al., "An Automated Methodology for Fetal Heart Rate Extraction from the Abdominal Electrocardiogram", 2006 IEEE.
(Continued)

*Primary Examiner* — Amanda K Hulbert

(57) ABSTRACT

According to an aspect, there is provided a device for measuring a physiological characteristic of a first subject, the device comprising a first electrode for contacting a part of the body of the first subject; a second electrode for contacting a part of the body of a second subject; and a control unit for obtaining an electrocardiogram, ECG, signal using the electrodes and for processing the ECG signal to determine a measurement of a physiological characteristic of the first subject; wherein the signal comprises a first ECG signal component relating to the first subject and a second ECG signal component relating to the second subject, and
(Continued)

the control unit is configured to process the ECG signal obtained from the electrodes to extract the first ECG signal component relating to the first subject and to process the first ECG signal component to determine a measurement of the physiological characteristic of the first subject.

21 Claims, 10 Drawing Sheets

(51) Int. Cl.
    *A61B 5/021*     (2006.01)
    *A61B 5/0404*     (2006.01)
    *A61B 5/00*     (2006.01)
    *A61B 5/024*     (2006.01)
    *A61B 5/0452*     (2006.01)
    *A61B 5/0245*     (2006.01)
    *A61B 5/0408*     (2006.01)

(52) U.S. Cl.
    CPC ........ *A61B 5/02427* (2013.01); *A61B 5/0404* (2013.01); *A61B 5/0408* (2013.01); *A61B 5/04012* (2013.01); *A61B 5/0452* (2013.01); *A61B 5/746* (2013.01)

(58) Field of Classification Search
    CPC ... A61B 5/0404; A61B 5/0408; A61B 5/0452; A61B 5/0456; A61B 5/14542; A61B 5/746; A61B 7/04
    See application file for complete search history.

(56) References Cited

U.S. PATENT DOCUMENTS

| | | |
|---|---|---|
| 2010/0081946 A1 | 4/2010 | Garudadri |
| 2010/0256509 A1 | 10/2010 | Kuo |
| 2013/0281868 A1* | 10/2013 | Kawachi ............ A61B 5/02141 600/485 |
| 2014/0120876 A1 | 5/2014 | Shen |
| 2014/0257056 A1 | 9/2014 | Moon |

FOREIGN PATENT DOCUMENTS

| | | |
|---|---|---|
| KR | 20060111159 | 10/2006 |
| KR | 101335107 | 8/2013 |
| WO | 2013066642 | 5/2013 |

OTHER PUBLICATIONS

Sato, et al., "A Novel Extraction Method of Fetal Electrocardiogram From the Composite Abdominal Signal", IEEE Transactions on Biomedical Engineering, vol. 54, No. 1, Jan. 2007.

* cited by examiner

| Physiological parameters | 3 | 2 | 1 | 0 | 1 | 2 | 3 |
|---|---|---|---|---|---|---|---|
| Respiration rate, bpm | ≤ 8 | | 9 - 11 | 12 - 20 | | 21 - 24 | ≥ 25 |
| Oxygen saturations % | ≤ 91 | 92 - 93 | 94 - 95 | ≥ 96 | | | |
| Any supplemental oxygen | | Yes | | No | | | |
| Temperature (°C) | ≤ 35.0 | | 35.1 - 36.0 | 36.1 - 38.0 | 38.1 - 39.0 | ≥ 39.1 | |
| Systolic BP (mmHg) | < 90 | 91 - 100 | 101 - 110 | 111 - 219 | | | ≥ 220 |
| Heart rate (bpm) | ≤ 40 | | 41 - 50 | 51 - 90 | 91 - 110 | 111 - 130 | ≥ 131 |
| Level of consciousness | | | | A | | | V, P, or U |

FIG. 13

DEVICE AND METHOD FOR MEASURING A PHYSIOLOGICAL CHARACTERISTIC OF A SUBJECT

CROSS REFERENCE TO RELATED APPLICATIONS

This application is the U.S. National Phase application under 35 U.S.C. § 371 of International Application No. PCT/EP2015/079179, filed Dec. 10, 2015, published as WO 2016/091984 on Jun. 16, 2016, which claims the benefit of European Patent Application Number 14197715.7 filed Dec. 12, 2014. These applications are hereby incorporated by reference herein.

TECHNICAL FIELD OF THE INVENTION

The invention relates to a device for measuring a physiological characteristic of a subject from an electrocardiogram (ECG) signal and a method of operating the same.

BACKGROUND TO THE INVENTION

Lowered blood pressure (BP) is considered an important indicator of dehydration or changed cardiovascular function, but a spot-check is often omitted due to the measurement requirements, which involve applying an inflatable cuff around the arm. As a surrogate for BP, a pulse arrival time (PAT) can be measured, which eliminates the need for a cuff. PAT is measured as the time between an R-peak in an electrocardiogram (ECG) and the foot of the arterial pulse pressure wave, commonly measured peripherally (e.g. on a limb) using photoplethysmography (PPG). At least three electrodes are normally required for PAT measurements, and these electrodes are placed on the chest or on both wrists and one ankle, with a PPG sensor on, for example, the finger, ear or forehead.

Devices are available (for example as shown on www.scanadu.com) that integrate ECG and PPG measurements into a single cableless device. These devices comprise two ECG electrodes, one of which is to be contacted by a finger of the subject (the user of the device) and the other is to be in contact with the forehead of the subject. The device also includes a PPG sensor that performs a PPG measurement at the forehead. The device measures the ECG potential between the finger and forehead (via the conductive loop established between the device, the finger and the subject's arm, chest, neck and head) and also the PPG at the forehead.

Although this device is useful for monitoring the PAT and PAT-derived blood pressure of the subject, it requires the finger and forehead of the subject to be in contact with the ECG electrodes, which means the device must be operated by the subject themselves, or, at the very least, the subject needs to be otherwise cooperative in using the device. For a subject that is unconscious (including sleeping or sedated) or otherwise uncooperative (e.g. a small child or physically or mentally challenged patients), this type of device cannot be used. It is not possible for the device to be operated by another person (e.g. a doctor, nurse, caregiver or family member) to obtain the measurements of the subject (e.g. a patient).

SUMMARY OF THE INVENTION

To address the problem of an uncooperative or unconscious subject, there is a need for a simple, easy-to-use device that can measure a physiological characteristic of a subject from an ECG signal (for example PAT or PAT-derived blood pressure) and that is operated or operable by another person, such as a doctor, nurse, caregiver, family member, etc. This can enable the other person to perform a spot check of the physiological characteristic of the subject. In the following, the term 'first subject' refers to the person whose physiological characteristic is being measured, and the term 'second subject' refers to the person involved in the operation of the device to obtain the physiological characteristic measurement of the first subject.

Thus, it is desirable to provide a device that can be operated by the second subject to obtain a measurement of a physiological characteristic for the first subject from an ECG signal for the first subject.

According to a first aspect, there is provided a device for measuring a physiological characteristic of a first subject, the device comprising a first electrode for contacting a part of the body of the first subject; a second electrode for contacting a part of the body of a second subject; and a control unit for obtaining an electrocardiogram, ECG, signal using the electrodes and for processing the ECG signal to determine a measurement of a physiological characteristic of the first subject; wherein the signal comprises a first ECG signal component relating to the first subject and a second ECG signal component relating to the second subject, and the control unit is configured to process the ECG signal obtained from the electrodes to extract the first ECG signal component relating to the first subject and to process the first ECG signal component to determine a measurement of the physiological characteristic of the first subject.

In some embodiments the first ECG signal component comprises R-peaks relating to the first subject and the second ECG signal component comprises R-peaks relating to the second subject.

In some embodiments the control unit is configured to process the ECG signal to identify at least a first set of R-peaks corresponding to one of the first subject and second subject.

In some embodiments the control unit is configured to identify the first set of R-peaks as one of (i) the maxima or maxima above a threshold value in the ECG signal; and (ii) the minima or minima below a threshold value in the ECG signal.

In some embodiments the control unit is further configured to identify a second set of R-peaks corresponding to the other one of the first subject and second subject as one of (i) the maxima or maxima above a threshold value in the ECG signal; and (ii) the minima or minima below a threshold value in the ECG signal.

In other embodiments the device further comprises a sensor for measuring a second physiological characteristic of one of the first subject and second subject.

In some embodiments the sensor is located close to the electrode for the one of the first subject and second subject such that the sensor measures the second physiological characteristic of the one of the first subject and second subject when the part of the body of the subject is in contact with the electrode.

In some embodiments the sensor is for measuring a photoplethysmography, PPG, signal of the first subject and the control unit is configured to use the PPG signal to determine the blood pressure of the first subject from the extracted first ECG signal component.

In some embodiments the control unit is configured to use the PPG signal and the extracted first ECG signal component to determine the pulse arrival time for the first subject, and to determine the blood pressure of the first subject from the pulse arrival time.

In some embodiments the control unit is configured to use the measurement of the second physiological characteristic to extract the first ECG signal component relating to the first subject from the ECG signal.

In some embodiments the second physiological characteristic is a physiological characteristic that can also be derived from the ECG signal.

In some embodiments the control unit is configured to extract the first ECG signal component relating to the first subject by deriving a value for the second physiological characteristic for one or both of the first subject and second subject from the ECG signal; comparing the value or values for the second physiological characteristic derived from the ECG signal to the measurement of the second physiological characteristic for said one of the first subject and second subject from the sensor; and identifying the ECG signal component in the ECG signal that has a value for the second physiological characteristic closest to the measurement from the sensor as that corresponding to said one of the first subject and second subject.

In some embodiments the control unit is configured to extract the first ECG signal component relating to the first subject by correlating the value or values for the second physiological characteristic with the ECG signal; and using the result of the correlation to identify an ECG signal component in the ECG signal corresponding to one of the first subject and second subject.

In some embodiments the second physiological characteristic is any one or more of heart rate, heart rate variability or the timing of heart beats.

In some embodiments the sensor is for measuring a photoplethysmography, PPG, signal of the one of the first subject and second subject, and the control unit is configured to extract the first ECG signal component as the R-peaks in the ECG signal that correspond to peaks in the PPG signal.

In some embodiments the device further comprises a second sensor for measuring the second physiological characteristic of the other one of the first subject and second subject.

In some embodiments the second sensor is located close to the electrode for the other one of the first subject and second subject such that the sensor measures the second physiological characteristic of the other one of the first subject and second subject when the part of the body of the subject is in contact with the electrode.

In some embodiments the control unit is configured to use the measurement of the second physiological characteristic from the second sensor to extract the first ECG signal component relating to the first subject from the ECG signal.

In some embodiments the control unit is further configured to obtain a second ECG signal for the second subject using the electrodes prior to obtaining the first ECG signal that comprises the first ECG signal component relating to the first subject and the second ECG signal component relating to the second subject, and to use the second ECG signal for the second subject or one or more physiological characteristics derived therefrom to process the first ECG signal to extract the first ECG signal component relating to the first subject.

In some embodiments the control unit is configured to process the first ECG signal component to determine a measurement of the heart rate or heart rate variability of the first subject.

In some embodiments the control unit is configured to analyse the ECG signal to determine if it contains ECG signal components for the first subject and the second subject, and to provide feedback to the second subject if the ECG signal contains an ECG signal component for just one subject.

In some embodiments the control unit is configured to analyse the ECG signal to determine if it contains ECG signal components for the first subject and the second subject by determining if the ECG signal contains two sets of R-peaks that have opposite polarities to each other.

In some embodiments the control unit is configured to analyse the ECG signal to determine if it contains ECG signal components for the first subject and the second subject by analysing the frequency spectrum of the ECG signal to identify if the ECG signal contains ECG signal components with different heart rates.

In some embodiments the control unit is configured to provide feedback to the second subject indicating that the device is being used incorrectly and/or that instructs the second subject in a correct way to use the device.

In some embodiments the device comprises a housing and the first electrode and second electrode are in fixed positions on an external surface of the housing.

In some embodiments the second electrode is arranged on the external surface of the housing such that a part of the body of the second subject will be in contact with the second electrode when the device is being held in the hand of the second subject.

In some embodiments the first electrode is arranged on the external surface of the housing such that it can be placed in contact with a part of the body of the first subject by the second subject when the device is being held in the hand of the second subject.

In some embodiments the part of the body of the first subject is the forehead, neck, shoulder or chest, and the part of the body of the second subject is a finger, thumb or other part of the hand.

According to a second aspect, there is provided a method of operating a device to measure a physiological characteristic of a first subject, the method comprising obtaining an electrocardiogram, ECG, signal using a first electrode that is in contact with a part of the body of the first subject and a second electrode that is in contact with a part of the body of a second subject, wherein the ECG signal comprises a first ECG signal component relating to the first subject and a second ECG signal component relating to the second subject; processing the ECG signal to extract the first ECG signal component relating to the first subject; and processing the first ECG signal component to determine the physiological characteristic of the first subject.

In some embodiments the first ECG signal component comprises R-peaks relating to the first subject and the second ECG signal component comprises R-peaks relating to the second subject.

In some embodiments the step of processing comprises processing the ECG signal to identify at least a first set of R-peaks corresponding to one of the first subject and second subject.

In some embodiments the step of processing comprises identifying the first set of R-peaks as one of (i) the maxima or maxima above a threshold value in the ECG signal; and (ii) the minima or minima below a threshold value in the ECG signal.

In some embodiments the step of processing comprises identifying a second set of R-peaks corresponding to the other one of the first subject and second subject as one of (i)

the maxima or maxima above a threshold value in the ECG signal; and (ii) the minima or minima below a threshold value in the ECG signal.

In some embodiments the method further comprises the step of measuring a second physiological characteristic of one of the first subject and second subject using a sensor.

In some embodiments the sensor is located close to the electrode for the one of the first subject and second subject such that the sensor measures the second physiological characteristic of the one of the first subject and second subject when the part of the body of the subject is in contact with the electrode.

In some embodiments the sensor is for measuring a photoplethysmography, PPG, signal of the first subject and the step of processing comprises using the PPG signal to determine the blood pressure of the first subject from the extracted first ECG signal component.

In some embodiments the method further comprises the steps of using the PPG signal and the extracted first ECG signal component to determine the pulse arrival time for the first subject, and determining the blood pressure of the first subject from the pulse arrival time.

In some embodiments the step of processing comprises using the measurement of the second physiological characteristic to extract the first ECG signal component relating to the first subject from the ECG signal.

In some embodiments the second physiological characteristic is a physiological characteristic that can also be derived from the ECG signal.

In some embodiments the step of processing comprises deriving a value for the second physiological characteristic for one or both of the first subject and second subject from the ECG signal; comparing the value or values for the second physiological characteristic derived from the ECG signal to the measurement of the second physiological characteristic for said one of the first subject and second subject from the sensor; and identifying the ECG signal component in the ECG signal that has a value for the second physiological characteristic closest to the measurement from the sensor as that corresponding to said one of the first subject and second subject.

In some embodiments the step of processing comprises correlating the value or values for the second physiological characteristic with the ECG signal; and using the result of the correlation to identify an ECG signal component in the ECG signal corresponding to one of the first subject and second subject.

In some embodiments the second physiological characteristic is any one or more of heart rate, heart rate variability or the timing of heart beats.

In some embodiments the step of measuring comprises measuring a photoplethysmography, PPG, signal of the one of the first subject and second subject, and the step of processing comprises extracting the first ECG signal component as the R-peaks in the ECG signal that correspond to peaks in the PPG signal.

In some embodiments the method further comprises the step of measuring the second physiological characteristic of the other one of the first subject and second subject using a second sensor.

In some embodiments the second sensor is located close to the electrode for the other one of the first subject and second subject such that the sensor measures the second physiological characteristic of the other one of the first subject and second subject when the part of the body of the subject is in contact with the electrode.

In some embodiments the step of processing comprises using the measurement of the second physiological characteristic from the second sensor to extract the first ECG signal component relating to the first subject from the ECG signal.

In some embodiments the method further comprises the step of obtaining a second ECG signal for the second subject using the electrodes prior to obtaining the first ECG signal that comprises the first ECG signal component relating to the first subject and the second ECG signal component relating to the second subject, and the step of processing comprises using the second ECG signal for the second subject or one or more physiological characteristics derived therefrom to process the first ECG signal to extract the first ECG signal component relating to the first subject.

In some embodiments the step of processing comprises processing the first ECG signal component to determine a measurement of the heart rate or heart rate variability of the first subject.

In some embodiments the method further comprises the steps of analysing the ECG signal to determine if it contains ECG signal components for the first subject and the second subject, and providing feedback to the second subject if the ECG signal contains an ECG signal component for just one subject.

In some embodiments the step of analysing the ECG signal to determine if it contains ECG signal components for the first subject and the second subject comprises determining if the ECG signal contains two sets of R-peaks that have opposite polarities to each other.

In some embodiments the step of analysing the ECG signal to determine if it contains ECG signal components for the first subject and the second subject comprises analysing the frequency spectrum of the ECG signal to identify if the ECG signal contains ECG signal components with different heart rates.

In some embodiments the method further comprises the step of providing feedback to the second subject indicating that the device is being used incorrectly and/or that instructs the second subject in a correct way to use the device.

In some embodiments the part of the body of the first subject is the forehead, neck, shoulder or chest, and the part of the body of the second subject is a finger, thumb or other part of the hand.

According to a third aspect, there is provided a computer program product comprising a computer readable medium having computer readable code embodied therein, the computer readable code being configured such that, on execution by a suitable computer, processor or control unit, the computer, processor or control unit is caused to perform any of the method embodiments described above.

According to a fourth aspect, there is provided a method of using a device to measure a physiological characteristic of a first subject, the device comprising a first electrode and a second electrode, the method comprising creating a conductive loop between the first subject, the device and a second subject that is in control of the device by contacting the first electrode to a part of the body of the first subject, contacting the second electrode to a part of the body of the second subject and establishing contact between the first subject and the second subject; and operating the device to measure a physiological characteristic of the first subject from an electrocardiogram, ECG, signal obtained via the first electrode and second electrode, the ECG signal comprising a first ECG signal component relating to the first subject and a second ECG signal component relating to the second subject.

In some embodiments the step of establishing contact between the first subject and the second subject comprises the second subject holding a hand, arm or shoulder of the first subject.

In some embodiments the second subject contacts the second electrode with a finger, thumb, or other part of their left or right hand, and establishes contact with the first subject using the other hand of the second subject.

In some embodiments, when the second subject is contacting the second electrode with a finger, thumb or other part of their left hand, the right hand of the second subject establishes contact with the right hand, right arm or right shoulder of the first subject.

In some embodiments, when the second subject is contacting the second electrode with a finger, thumb or other part of their right hand, the left hand of the second subject establishes contact with the left hand, left arm or left shoulder of the first subject.

In some embodiments the step of operating the device comprises operating the device according to any of the method embodiments set out above.

In some embodiments the device is as described in any of the above device embodiments.

BRIEF DESCRIPTION OF THE DRAWINGS

For a better understanding of the invention, and to show more clearly how it may be carried into effect, reference will now be made, by way of example only, to the accompanying drawings, in which:

FIG. 13 is a table illustrating the National Early Warning Score of the Royal College of Physicians.

DETAILED DESCRIPTION OF THE PREFERRED EMBODIMENTS

As noted above, the term 'first subject' herein refers to the person whose physiological characteristic(s) is(are) being measured, and the term 'second subject' refers to the person involved in the operation of the device to obtain the physiological characteristic measurement of the first subject.

Briefly, a device is provided that can be operated by the second subject to obtain a measurement of a physiological characteristic for the first subject from an ECG measurement of the first subject. This ECG measurement is obtained via a conductive loop established by the second subject making contact with the first subject (for example by the second subject holding a hand of the first subject), a first electrode of the device that is placed in contact with the first subject (for example at their forehead, neck, shoulder or chest) and a second electrode of the device that is placed in contact with part of the second subject (for example a finger, thumb or palm of the hand). The contact between the second subject and the first subject that completes the conductive loop can be skin contact, which can be improved or optimised by one or both of the first subject and second subject wearing a conducting component at the point of contact. For example the first subject and/or second subject can wear a conducting glove or hold a conducting rod. It will also be appreciated that a conducting component, such as a conducting glove can also be worn by the second subject on the hand that is holding the device in order to improve the conductive contact with the second electrode of the device.

Provided that the heart of the first subject is part of this conductive loop (see for example FIG. 4 below), the device will measure an ECG potential or signal through the conductive loop that comprises a first ECG signal component that corresponds to the activity of the heart of the first subject and a second ECG signal component that corresponds to the activity of the heart of the second subject. The device processes the ECG signal to identify or extract the ECG signal component for the first subject, and then determines one or more physiological characteristics of the first subject from the extracted ECG signal component (this physiological characteristic is also referred to as an ECG-derived physiological characteristic herein).

Those skilled in the art will be aware of various physiological characteristics that can be determined or derived from an ECG signal for a subject. In certain embodiments, the physiological characteristic can be, for example, heart rate, heart rate variability or blood pressure (when combined with a measurement of the pulse arrival time (PAT) from another physiological characteristic sensor).

Figure 1:
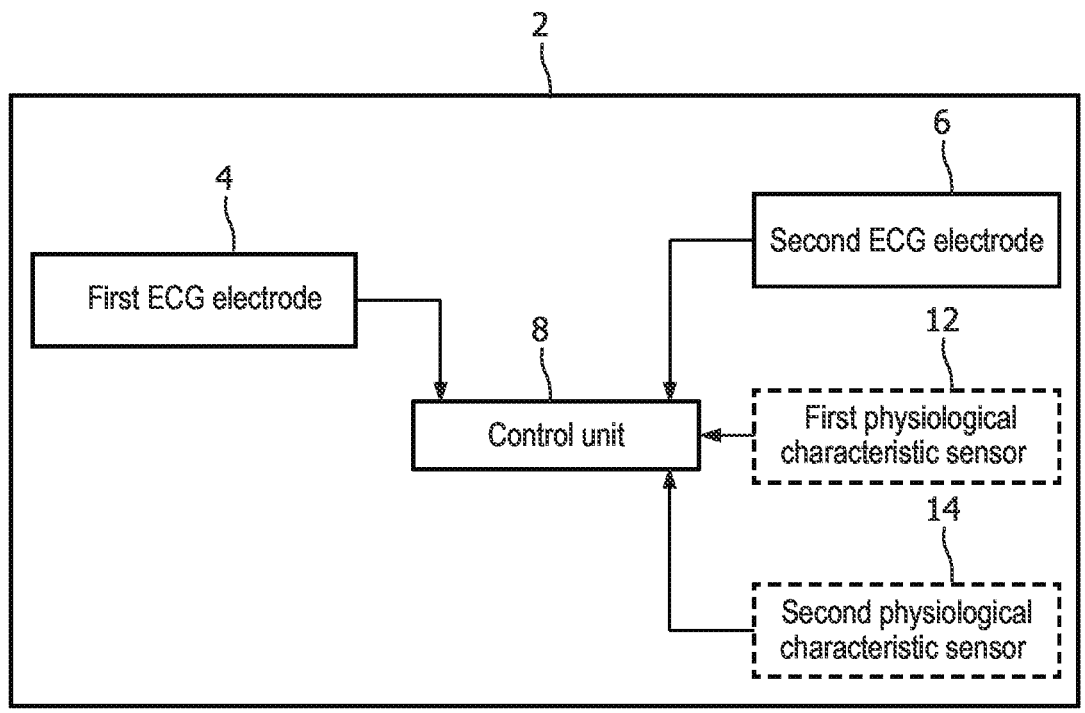
FIG. 1 is a block diagram of a device according to a first aspect of the invention.

FIG. 1 is a block diagram of a device 2 according to an aspect of the invention. The device 2 comprises a first electrode 4 and a second electrode 6 (also referred to as first ECG electrode 4 and second ECG electrode 6 respectively) that are connected to a control unit 8. The control unit 8 operates to measure an ECG potential or ECG signal through the first and second electrodes 4, 6 when a conductive loop is formed by the electrodes 4, 6 and the first and second subjects. The ECG potential or signal obtained through using the two ECG electrodes 4, 6 contains enough information to enable the timing of R-peaks to be detected and for other ECG characteristics to be detected.

The control unit 8 performs the analysis of the measured ECG potential or signal to determine the measurement of the physiological characteristic of the first subject according to the techniques described below. The control unit 8 can comprise one or more processors, processing units, multi-core processors or processing modules that are configured or programmed to control the device 2 and perform the analysis of the measured ECG signal described below. Although not shown in FIG. 1, the device 2 can further comprise a memory module for storing program code that can be executed by the control unit 8 to perform these operations. The memory module can also be used to store signal and measurements made or obtained by the device 2 during operation.

The first ECG electrode 4 and second ECG electrode 6 can be any suitable type of electrode for obtaining an ECG signal from a subject, and those skilled in the art will be aware of various types of electrodes that can be used in the device 2 according to the invention.

The first ECG electrode 4 is for contacting a part of the body of the first subject and the second ECG electrode 6 is for contacting a part of the body of the second subject.

In some embodiments, the first ECG electrode 4 and/or second ECG electrode 6 are attached to the control unit 8 via leads so that the first and/or second ECG electrodes 4, 6 can be readily attached to a desired part of the first subject and second subject respectively.

However, in preferred embodiments, the first ECG electrode 4 and second ECG electrode 6 are in fixed positions on the external surface of a housing of the device 2. In particularly preferred embodiments, the housing of the device 2 and the second ECG electrode 6 are arranged so that the second ECG electrode 6 is in contact with a part of the body of the second subject (for example one or more fingers of the second subject or the palm or back of the second subject's hand) when the device 2 is being held by the second subject, and the first ECG electrode 4 is arranged on the external surface of the housing so that it can be placed in contact with a part of the body of the first subject while the device 2 is being held by the second subject.

In either of the above embodiments, the first electrode 4 and second electrode 6 are galvanically separated from each other.

Figure 2:
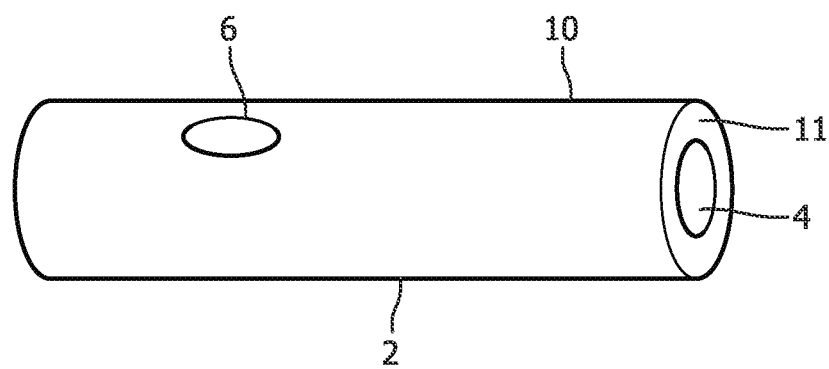
FIG. 2 is an illustration of a particular embodiment of a device according to the first aspect.

FIG. 2 illustrates a particular embodiment of a device 2 according to the above preferred embodiments. In this embodiment, the device 2 is formed into a shape that has dimensions similar to a standard pen or pencil. Thus, the housing 10 of the device 2 is generally cylindrical, with the first ECG electrode 4 being located on a face 11 at one end of the cylindrical housing 10 and the second ECG electrode 6 being located on the main body of the cylinder in a position that enables the second ECG electrode 6 to be contacted by a finger or thumb of the second subject when the device 2 is being held by the second subject. In alternative embodiments, the second ECG electrode 6, could, for example, be located at the opposite end of the cylindrical housing 10 to the face 11 carrying the first ECG electrode 4. In this alternative, it may be appropriate for the second subject to contact the second ECG electrode 6 using their thumb.

In alternative embodiments to that illustrated in FIG. 2, the device 2 could have the shape of or be formed as part of a mobile telephone, smart phone, tablet computer or other portable electronic device, with the first and second electrodes 4, 6 being arranged on the external surface of those devices in a suitable manner to enable the first electrode 4 to be contacted with the first subject and the second electrode 6 to be contacted with the second subject when the second subject is using the device 2. In some embodiments, the device 2 can be ergonomically designed so that it can only be comfortably held and used by one of the hands of the second subject (i.e. the left hand or right hand).

It will be appreciated that FIG. 1 only shows the components required to illustrate this aspect of the invention, and in a practical implementation the device 2 will comprise additional components to those shown. For example, the device 2 may comprise a battery or other power supply for powering the device 2, a communication module for enabling the measurements of the physiological characteristic(s) of the first subject to be communicated to a base unit for the device 2 or a remote computer, and/or one or more user interface components that allow a user (e.g. the second subject) to interact and control the device 2. As an example, the one or more user interface components could comprise a switch, a button or other control means for activating and deactivating the device 2 and/or measurement process. The user interface components can also or alternatively comprise a display or other visual indicator for providing information to the second subject and/or first subject about the operation of the device 2, including displaying the measurements of the physiological characteristic(s).

In addition, as described in more detail below, the device 2 may also comprise one or more sensors for measuring one or more other physiological characteristics of the first subject and/or the second subject (i.e. one or more physiological characteristics other than that to be obtained from the ECG signal of the first subject). In some embodiments, the measurements from this or these sensors can provide additional information on the health of the first subject (i.e. additional to the information provided by the measurement of the physiological characteristic obtained from the ECG signal), and can include, for example, the temperature or breathing rate of the first subject. However, in preferred embodiments (which are also described in more detail below), the measurement of the one or more other physiological characteristics of the first subject and/or second subject can be used by the control unit 8 in the extraction of the ECG signal component relating to the first subject from the ECG signal. Suitable physiological characteristics include, but are not limited to, the heart rate, the specific times at which the heart beats, heart rate variability, and the pulse arrival time.

A first physiological characteristic sensor 12 and second physiological characteristic sensor 14 are shown in dashed boxes in FIG. 1 (which indicates that they are optional features). It will be appreciated that in certain embodiments only one physiological characteristic sensor may be provided in the device 2, and in other embodiments there may be more than the two physiological characteristic sensors shown. These sensors 12 and 14 may be used to measure a particular physiological characteristic or characteristics of one or both of the first subject and the second subject. In some embodiments, each sensor can be co-located with an electrode 4, 6 or otherwise located on the device 2 so that the sensor can take a measurement of the physiological characteristic when the first subject or second subject (as appropriate) is in contact with the electrode and an ECG signal is being obtained via the electrodes 4, 6.

In some embodiments, the physiological characteristic sensor(s) 12, 14 can comprise any of a photoplethysmography (PPG) sensor, an (near-)infrared light source and/or sensor, a blood oxygen saturation (SpO2) sensor, a thermometer and a microphone (for example for measuring heart sounds).

Figure 3:
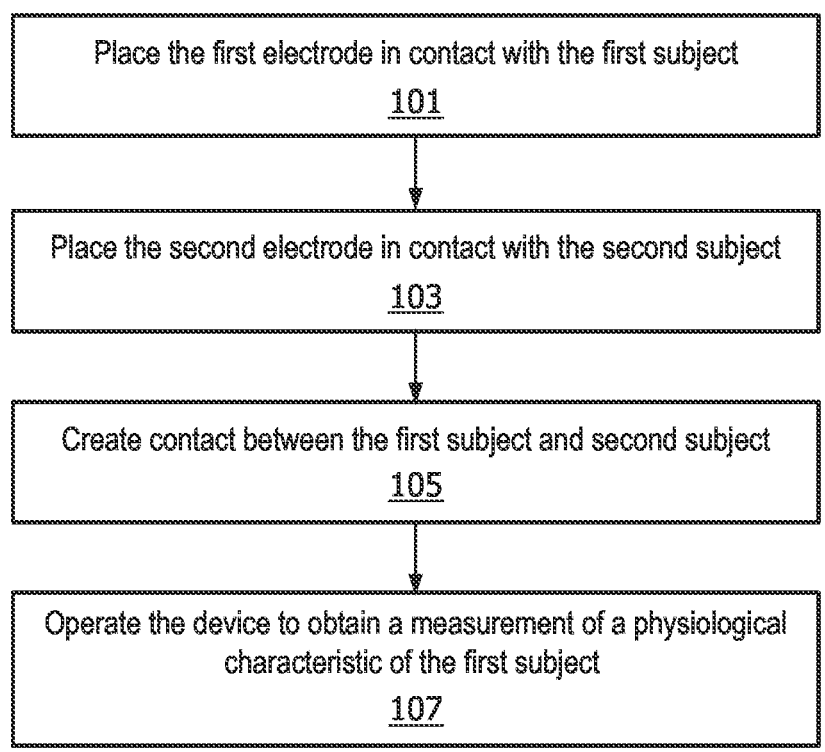
FIG. 3 is a flow chart illustrating a method of using a device according to the invention to measure a physiological characteristic of a first subject.

The flow chart in FIG. 3 illustrates a method of using a device 2 as described above to measure a physiological characteristic of a first subject. This method is typically performed by the second subject. In a first step, step 101, the second subject places the first electrode 4 in contact with a part of the body of the first subject. In the next step, step 103, the second subject contacts the second electrode 6 with a part of their body. In step 105, the second subject creates contact with the first subject, for example by holding their hand. As noted above, this contact completes a conductive loop between the first subject, the second subject and the device 2. The contact between the first subject and the second subject can be skin contact, although the conductivity of the contact can be optimised or improved by one or both of the first subject and second subject wearing a conducting component at the point of contact. For example the first subject and/or second subject can wear a conducting glove or hold a conducting rod.

Thus, following steps 101, 103 and 105 (which can be performed in any order, not just the order shown in FIG. 3), a conductive loop between the first subject, the device and a second subject will be created that enables an ECG signal to be measured by the device 2.

In the next step, step 107, the second subject operates the device 2 to measure a physiological characteristic of the first subject. As noted above, and as described in more detail below, operating the device 2 results in an ECG signal being obtained via the first electrode and second electrode that includes a first ECG signal component relating to the first subject and a second ECG signal component relating to the second subject, with the device 2 extracting the first ECG signal component and determining the measurement of the physiological characteristic from the extracted first ECG signal component.

Figure 4:
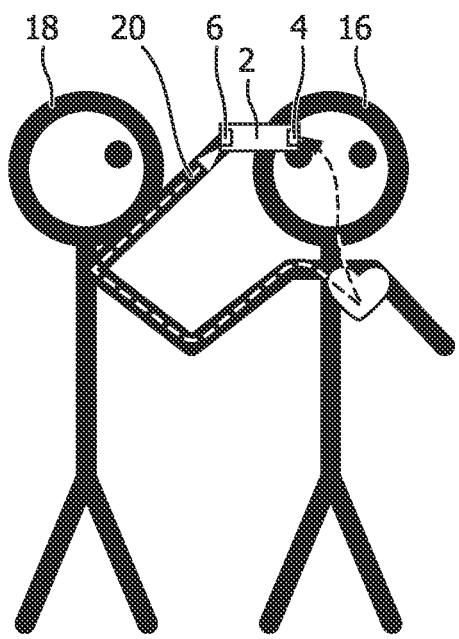
FIG. 4 is a diagram illustrating a device according to the first aspect in use by a first subject and a second subject.

FIG. 4 illustrates an exemplary use of a device 2 to measure a physiological characteristic of a first subject 16 by a second subject 18. Thus, the second subject 18 is holding the device 2 so that their finger or thumb is in contact with the second electrode 6 (following step 103) and they are holding the first electrode 4 against the forehead of the first subject 16 (following step 101). The second subject 18 is also holding the hand of the first subject 16 (following step 105) so that this skin contact creates the conductive loop required to obtain an ECG signal containing ECG signal components from both subjects using the electrodes (although as noted above a conducting component may be used to improve the contact between the subjects 16, 18. The conductive loop is indicated in FIG. 4 by dashed arrow 20. It will be appreciated that other locations for the skin contact and contact between the first electrode 4 and the first subject 16 are possible, provided that the heart of the first subject 16 is in the conductive loop 20 (i.e. between the contact points).

In some embodiments, as described in more detail later, to enable the ECG signal component for the first subject 16 to be extracted from the measured ECG signal, it is necessary for the conductive loop 20 to be formed in a particular manner. For example, when the second subject 18 is holding the device 2 with their left hand, their right hand should hold or otherwise be in contact with the right hand, right arm or right shoulder of the first subject 16. This configuration is illustrated in FIG. 4. As noted above, it will be appreciated that other locations for the contact and contact between the first electrode 4 and the first subject 16 are possible, provided that the heart of the first subject 16 is in the conductive loop 20 (i.e. between the contact points). So, for example, other locations on the right side of the first subject 16 or below the heart of the first subject 16 are possible.

The opposite configuration to that shown in FIG. 4 is also possible (so the second subject 18 holds the device 2 with their right hand, and their left hand should hold or otherwise be in contact with the left hand, left arm or left shoulder of the first subject 16.

In other embodiments where the control unit 8 executes a different algorithm for extracting the first ECG signal component for the first subject 16 from the measured ECG signal (which is also described in more detail below), there are less restrictions on how the second subject 18 should create the conductive loop 20 with the first subject 16. In particular, provided that the second subject 18 contacts the first subject 16 with the first electrode 4 and obtains contact with the first subject 16 in such a way that the heart of the first subject 16 is in the conductive loop 20 between the device 2 and the second subject's hand (or other body part that is in contact with the first subject 16), which includes either of the configurations described in the preceding two paragraphs, the obtained ECG signal will include an ECG signal component for the first subject 16 that can be analysed to determine the measurement of the physiological characteristic.

Incorrect use of the device 2 by the second subject 18 in which the heart of the first subject 16 is not in the conductive loop 20 will result in the measured ECG signal only including ECG information for the second subject 18, and it will mean that it is not possible determine the measurement of the physiological characteristic of the first subject 16.

Figure 5:
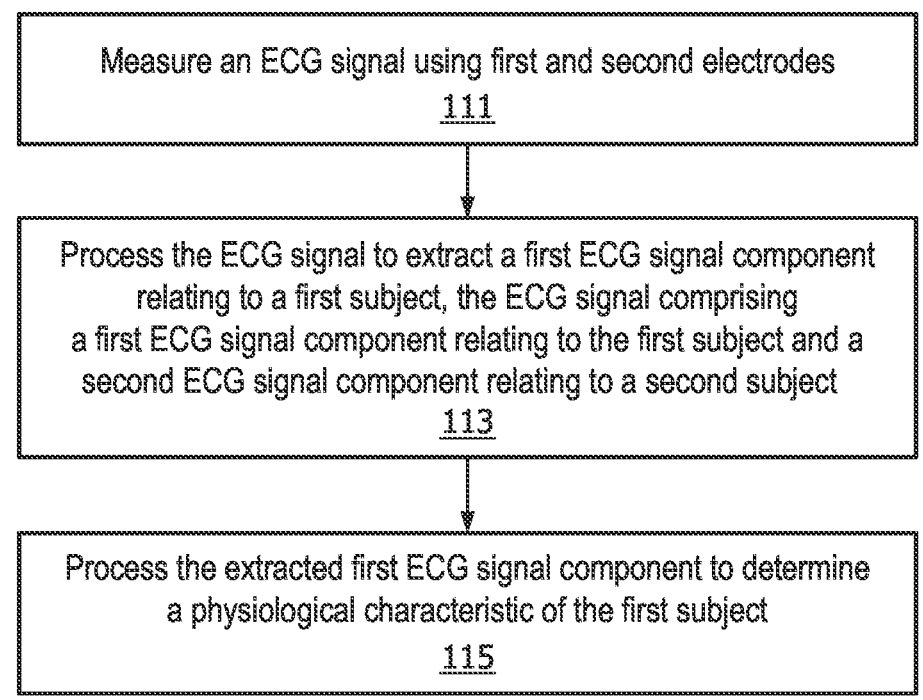
FIG. 5 is a flow chart illustrating a method of operating a device according to the invention to measure a physiological characteristic of a first subject.

FIG. 5 is a flow chart that illustrates the operation of the device 2 according to an aspect of the invention. It will be appreciated that the steps in the method of FIG. 5 are generally performed by, or under the control of, the control unit 8.

In step 111, when the device 2 is activated and a conductive loop 20 exists between the first electrode 4 and second electrode 6, the device 2 measures an ECG signal (i.e. the electrical potential between the electrodes 4, 6). Provided that the conductive loop 20 has been formed by the second subject 18 with the device 2 and the first subject 16 in the correct manner, the ECG signal measured by the device 2 will include a first ECG signal component relating to the first subject and a second ECG signal component relating to the second subject. That is, the measured ECG signal is a composite signal of an ECG signal for the first subject (i.e. a signal representing the electrical activity of the heart of the first subject) and an ECG signal for the second subject (i.e. a signal representing the electrical activity of the heart of the first subject).

The ECG signal is measured by the device 2 over a period of time, for example a few seconds, or enough time to cover a few heart beats in the first subject 16, which provides an ECG signal of sufficient length to enable the physiological characteristic of the first subject to be determined.

Once the ECG signal has been measured, the control unit 8 processes the ECG signal to extract the first ECG signal component relating to the first subject (step 113). Preferably, step 113 comprises identifying ECG signal R-peaks in the ECG signal, and identifying the R-peaks that correspond to the first subject 16 in the ECG signal.

Various embodiments of step 113 are described in more detail below.

In step 115 the extracted first ECG signal component is processed to determine the required physiological characteristic of the first subject 16. In preferred embodiments, the required physiological characteristic is determined from the identified R-peaks for the first subject 16.

Figure 6:
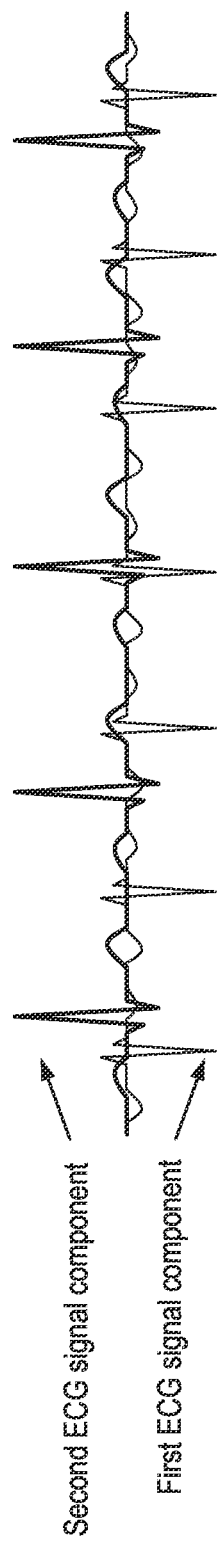
FIG. 6 illustrates two ECG signal components for different subjects drawn over the top of each other.

Some exemplary techniques for performing step 113 (processing the ECG signal to extract a first ECG signal component relating to the first subject 16) are now described:

The simplest technique for performing step 113 requires the conductive loop 20 to be established between the first subject 16, second device 18 and device 2 as shown in FIG. 4 or the opposite configuration where the second subject 18 holds the device 2 with their right hand, and their left hand is holding or otherwise in contact with the left hand, left arm or left shoulder of the first subject 16. FIG. 6 illustrates two ECG signal components for different subjects drawn over the top of each other (so it will be appreciated that the ECG signal actually measured by the device 2 will be a composite of these ECG signal components). An exemplary composite ECG signal measured by the device 2 in this configuration is shown in the bottom left trace of FIG. 9. With this configuration of the conductive loop 20, the R-peaks in the ECG signal component relating to the first subject 16 will point in the opposite direction to the R-peaks in the ECG component relating to the second subject 18 (in other words the ECG signal component for the first subject 16 is the opposite polarity to the ECG signal component for the second subject 18). In particular, when the right hand of the second subject 18 is holding the right hand (or right arm or right shoulder) of the first subject 16 as shown in FIG. 4, the R-peaks for the first subject 16 point downwards and the R-peaks for the second subject 18 point upwards, which can be seen in FIGS. 6 and 9. In the opposite configuration to that shown in FIG. 4 (where the left hand of the second subject 18 is holding the left hand, left arm or left shoulder of the first subject 16) the R-peaks for the first subject 16 point upwards and the R-peaks for the second subject 18 point downwards.

Thus, in the simplest technique for performing step 113, the control unit 8 analyses the ECG signal to identify the R-peaks for the first subject 16 as the peaks in the ECG signal that are pointing in the appropriate direction for the first subject 16 (or having the appropriate polarity). The appropriate direction can be determined based on knowledge of the configuration of the conductive loop between the first subject 16 and the second subject 18, for example based on an input to the device 2 by the second subject 18, or by configuring the shape of the device 2 so that it can only be comfortably operated by a particular hand of the second subject 18 (i.e. by ergonomically shaping the device 2 so that it fits the left or right hand).

In one embodiment, the R-peaks can be identified by finding the maxima or local maxima in the ECG signal (or maxima that have an amplitude above a threshold value to avoid every local maxima in the ECG signal being considered an R-peak). It will be appreciated that this technique can alternatively identify the R-peaks for the second subject 18 using an analysis similar to that described above, but where the minima or local minima (below a threshold value to avoid all minima being identified as R-peaks) in the ECG signal are identified. In an alternative embodiment, R-peaks can be detected by analysing the sequence of characteristics in the ECG signal. In particular, R-peaks follow a P wave, so an R-peak can be detected as the peak following a detected P wave. In a further alternative embodiment, R-peaks can be detected by using more sophisticated signal processing techniques, such as those based on wavelet transformation.

If the second subject 18 establishes the conductive loop 20 with the heart of the first subject 16 in the loop 20 but does not contact the first subject 16 as shown in FIG. 4 or the opposite configuration where the left hand of the second subject 18 contacts the left hand (or left arm or left shoulder) of the first subject 16, then the ECG signal will contain ECG signal components for both the first subject 16 and the second subject 18, but the ECG characteristics of the ECG signal components will be oriented the same way (i.e. the R-peaks of both signal components will have the same polarity), which means that it is not possible to identify the ECG signal component corresponding to the first subject 16 simply by identifying the maxima and/or minima according to the technique described above.

Therefore, in some embodiments, if the control unit 8 is not able to extract an ECG signal component from the ECG signal (e.g. if the control unit 8 determines that the R-peaks all point in the same way or cannot identify R-peaks in both directions (i.e. they all have the same polarity)), the control unit 8 can provide feedback to the second subject 18 indicating that the device 2 is not being used correctly or that the second subject 18 needs to contact the first subject 16 differently (for example the second subject 18 needs to hold the other hand or arm of the first subject 16). This feedback can be provided visually, for example via a user interface (e.g. a display or warning lights) and/or audibly (e.g. via a speaker). In some cases the feedback can simply be an indication that there is an error or that the device 2 is not being used correctly, but in other cases the feedback can comprise an instruction or advice to hold the device 2 and/or contact the first subject 16 differently or in a particular manner.

In a more preferable technique for performing step 113, a measurement of a physiological characteristic of the first subject or second subject obtained using a separate sensor to the ECG signal is used to identify the required ECG signal component in the ECG signal. Preferably the measurement obtained with the separate sensor is a measurement of a physiological characteristic that can also be derived from an ECG signal, since this means that the measurement can be used to help distinguish between the ECG signal components in the measured ECG signal (which should have different values for the physiological characteristic since they are obtained from different subjects). This technique can be used when the conductive loop 20 is established as shown in FIG. 4 or the opposite configuration, and, in some implementations, can also be used when the second subject 18 is holding the opposite hand or side of the first subject 16 (i.e. the left hand of the second subject 18 is holding the right hand of the first subject 16, and vice versa) so the R-peaks are all pointing in the same direction.

Figure 7:
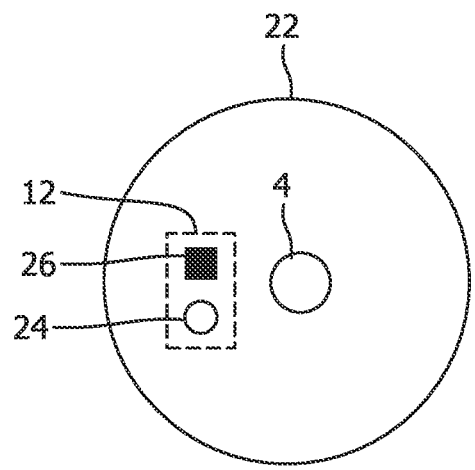
FIG. 7 is an illustration of a first exemplary sensor array.

Thus, this technique requires the device 2 to comprise at least a first physiological characteristic sensor 12 that is arranged to measure a physiological characteristic of one of the first subject and second subject as the ECG signal is being measured. In some embodiments, the first physiological characteristic sensor 12 can be located close to the appropriate electrode 4, 6 so that when the electrode 4, 6 is in contact with the appropriate subject, the sensor 12 can measure the physiological characteristic. An exemplary sensing array 22 is shown in FIG. 7, with the additional sensor 12 being a PPG sensor that is arranged close to the first electrode 4 so that it can measure a PPG signal for the first subject 16. As appreciated by those skilled in the art, the PPG sensor 12 can comprise a light source 24 and a light sensor 26 (such as a photodetector) that is sensitive to at least the wavelength(s) of light emitted by the light source 24. In an exemplary, non-limiting, implementation, the light source can be a green light emitting diode (LED) that emits light at wavelengths in the range of 500-600 nm and the photodetector can be sensitive to light at wavelengths below 1000 nm.

Figure 8:
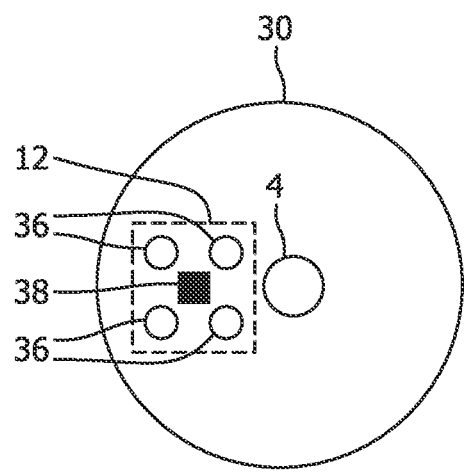
FIG. 8 is an illustration of a second exemplary sensor array.

Another exemplary sensing array 30 is shown in FIG. 8, which comprises an additional sensor 12 in the form of an SpO2 sensor (i.e. a blood oxygen saturation sensor). In this example, the SpO2 sensor 12 comprises a plurality of light sources 36 (four in the illustrated embodiment) and a light sensor 38 that is sensitive to at least the wavelengths of light emitted by the light sources 36. The light sources 36 can include, for example, a near-infrared LED that emits light at wavelengths in the range of 800-1000 nm and a red LED that emits light at wavelengths in the range of 600-700 nm, and the light sensor 38 can be sensitive to light at wavelengths below 1000 nm.

Figure 9:
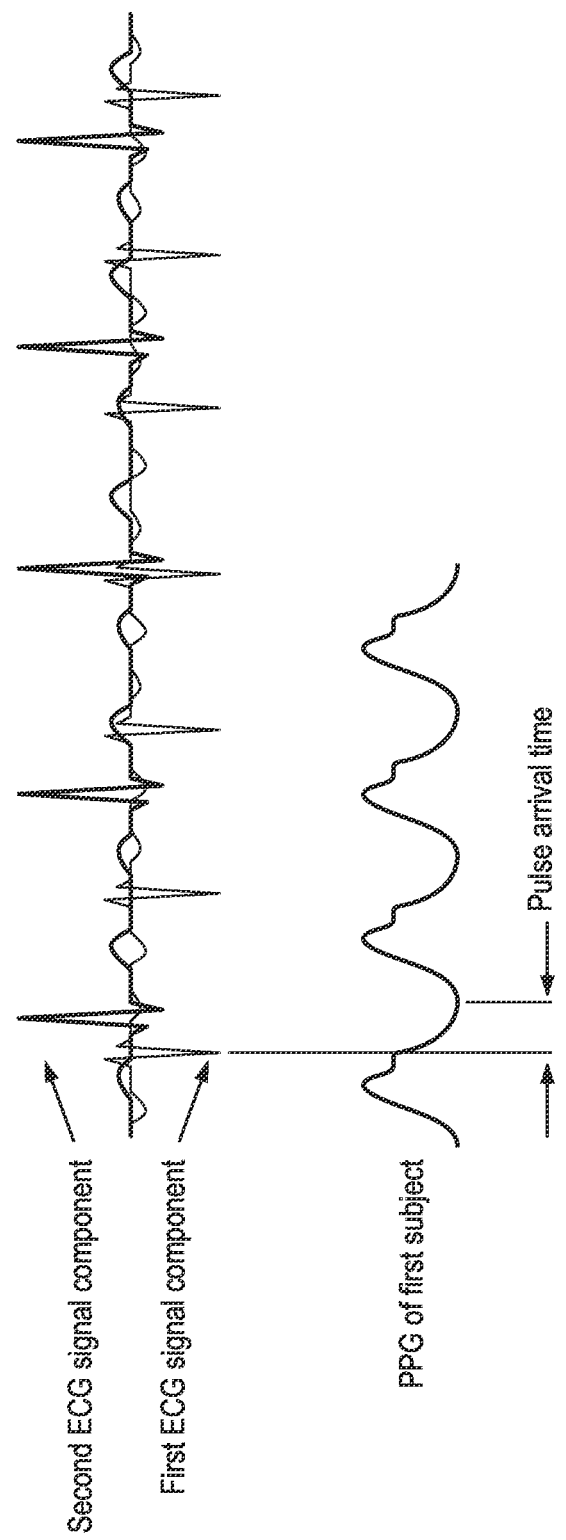
FIG. 9 illustrates two ECG signal components for different subjects drawn over the top of each other and a PPG signal for a first subject.
Figure 10:
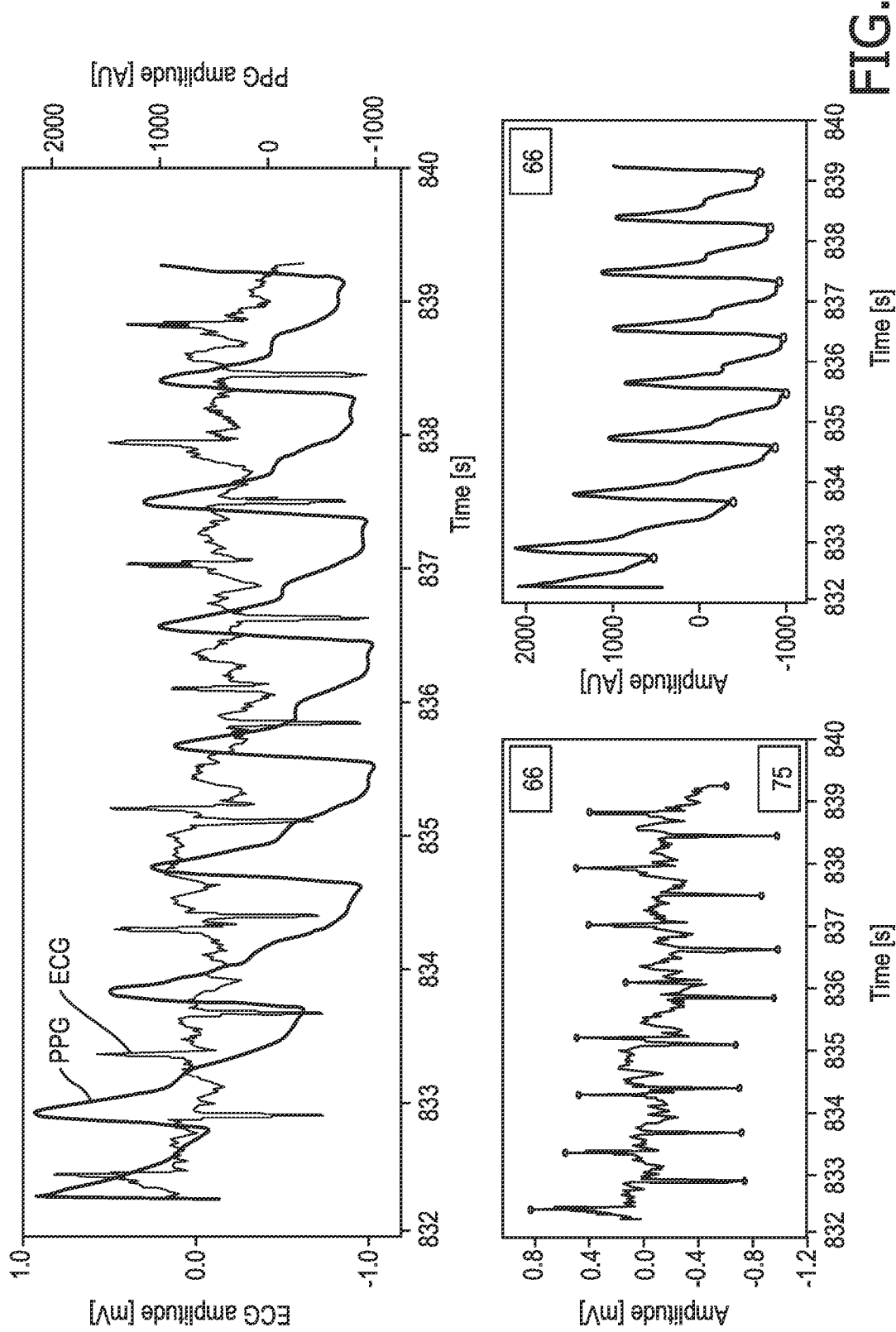
FIG. 10 shows an exemplary ECG signal and PPG signal obtained by a device according to the invention.

FIG. 9 illustrates the ECG signal components from FIG. 6 along with an exemplary PPG signal for the first subject 16. FIG. 10 shows an exemplary measured ECG signal in the bottom left trace (with the R-peaks for the two subjects in opposite directions; although it will be appreciated that this is not required in this technique), an exemplary measured PPG signal for the first subject in the bottom right trace, and the measured ECG signal and PPG signal superposed into a single view (the top trace in FIG. 10).

As noted above, a measurement of a physiological characteristic of the first subject or second subject obtained using the separate sensor 12 (which is also referred to as an 'additional measurement' herein) is used to identify the required ECG signal component in the ECG signal. In some embodiments the additional measurement is a measurement of a physiological characteristic that can also be derived from an ECG signal, such as heart rate, heart rate variability, or the times at which heart beats occurred (for example as indicated by the timing of R-peaks in the ECG signal). This measurement can be obtained from a PPG signal, or any other suitable signal or type of sensor.

In one implementation of this more preferable technique, the ECG signal is analysed to identify R-peaks that correspond to the additional physiological characteristic measurement. For example, where the additional measurement is a measurement of the heart rate, the ECG signal can be analysed to identify the set of R-peaks that correspond to the same heart rate (or correspond most closely to that heart rate). It can be seen in FIG. 9 that a heart rate derived from the PPG signal most closely matches the frequency of the R-peaks in the downward direction, which, since the PPG signal was measured from the first subject 16 (since it is located close to the first electrode 4), indicates that the R-peaks in the downward direction correspond to those of the first subject 16. Likewise in FIG. 10, the heart rate for the set of 'upward' R-peaks is 66 bpm and the heart rate for the set of 'downward' R-peaks is 75 bpm, and since the PPG signal for the first subject 16 gives a heart rate of 66 bpm, it can be determined that the set of 'upward' peaks in the ECG signal are those relating to the first subject 16. The set of R-peaks that are found to relate to the first subject 16 can then be used in step 115 to determine the required physiological characteristic of the first subject 16 (e.g. PAT-derived blood pressure, where it is noted that the PATs obtained from the first subject's R-peaks and the PPG signal are shown on the right hand side of FIG. 10). Where the R-peaks of both subjects 16, 18 are pointing in the same direction, a cross-correlation of the additional measurement and the ECG signal (or a signal representing the appropriate parameter that is derived from the ECG signal) can be used to identify the parts of the ECG signal corresponding to the first subject 16 and the second subject 18.

In a similar manner, rather than explicitly calculate a heart rate for the ECG signal, the PPG signal for the first subject 16 can be compared to the ECG signal (for example as shown in the top trace in FIG. 10) to match each peak or minima in the PPG signal to an R-peak in the ECG signal (with the peaks that match the peaks/minima in the PPG signal forming the set of R-peaks for the first subject 16).

It will be appreciated that both of the above techniques can be combined to improve the robustness of the R-peak identification. Thus, in some implementations, the analysis can comprise identifying R-peaks from heart rates determined from the ECG signal and PPG signal and by matching peaks in the PPG signal to the peaks in the ECG signal.

In an alternative approach, the maxima and/or minima of the PPG signal can be identified, and a heart rate and heart rate variability can be determined from the maxima and/or minima. For all R-peaks in the ECG signal the PAT can be determined, and the R-peaks and/or corresponding PAT-values for the first subject 16 can be identified based on the heart rate, heart rate variability, PAT, and PAT variability.

It will be appreciated that in some embodiments the additional sensor 12 may be located near to the second electrode 6 that is to be contacted to the second subject 18 so that it measures the physiological characteristic of the second subject 18 rather than the first subject 16. In this case, the analysis is the same as that described above, but it will be appreciated that the set of R-peaks that correspond to the characteristics of the measurement from the additional sensor 12 will be those that correspond to the second subject 18, which means that the remaining R-peaks in the ECG signal can be assumed to correspond to the first subject 16.

It will be appreciated that this technique can also make use of the fact that the R-peaks of the first and second subjects may be in opposite directions (when the conductive loop 20 is established as shown in FIG. 4 or in the opposite configuration), in which case this technique may perform an initial 'separation' of the ECG signal into two ECG signal components (i.e. two sets of R-peaks), one for each subject, based on the direction of the R-peaks, and then use the measurement from the sensor 12 to determine which of the ECG signal components corresponds to the required subject.

In another embodiment, which can be used when the conductive loop 20 is established in any configuration (so when the R-peaks of the first and second subjects 16, 18 are in the same or opposite directions), the R-peaks of the first subject 16 can be identified by: (1) determining a pulse arrival time (PAT) for each R-peak based on the PPG signal (so determining a PAT for each R-peak regardless of whether it is for the first subject 16 or second subject 18; (2) determining the distribution of the determined PATs; (3) identifying a peak in the distribution that corresponds to the (average) mean PAT of the first subject 16 (since the PATs derived from the first subject's R-peaks, being synchronous with the PPG signal, are much more constant than the PATs derived from the R-peaks of the second subject 18 which are asynchronous with the PPG signal); (4) rejecting all R-peaks with a PAT that deviates by more than a threshold amount from the identified peak in the distribution; (5) rejecting all R-peaks that are irregular with respect to their (beat-to-beat) heart rate (variability). As in the other embodiments above, the blood pressure of the first subject 16 can then be determined by determining the distribution of PATs of the remaining R-peaks (which should be those of the first subject 16), identifying the peak in the distribution which corresponds to the first subject's mean PAT and relating the first subject's PAT to the first subject's blood pressure via a calibration function or table.

In a further embodiment of step 113, a separate physiological characteristic sensor is provided for each subject so that a measurement of the physiological characteristic is obtained for each subject. The additional sensors can be located near to the appropriate electrode 4, 6 so that the measurements can be made while the ECG signal is being obtained. The analysis in this embodiment is similar to that described above, but the availability of the measurement of the physiological characteristic for both subjects improves the accuracy of the identification of the R-peaks for each subject.

In a further embodiment (which can be used separate to or in combination with the techniques described above for separating the ECG signal components), the device 2 can make use of known ECG characteristics for the second subject in order to improve or enable the separation of the ECG signal component for the first subject 16 from the ECG signal. In particular, during a calibration phase, or otherwise just prior to using the device 2 to measure the physiological characteristic of the first subject 16, an ECG signal for the second subject 18 can be obtained (for example by the second subject 18 contacting the second electrode 6 with their hand and holding the first electrode 4 to their forehead, neck, chest or other hand) and stored. This ECG signal, or ECG or other physiological characteristics that can be derived from the ECG signal, can be used to identify the ECG signal component relating to the second subject 18 in an ECG signal that contains signal components for both subjects. The processing required here is similar to that described above for the other separation techniques that use a measurement of a physiological characteristic obtained from a separate sensor 12. It will be appreciated that in this embodiment, since an ECG signal can uniquely identify an individual (since an ECG can be a biometric), the ECG signal obtained for the second subject 18 prior to the use of the device 2 to measure a physiological characteristic of a first subject 16 can be used to identify the particular second subject 18 that is using the device 2, and this information can be used, for example, to assist in linking the measured physiological characteristic for a first subject 16 to an appropriate medical file.

In some of the above embodiments, prior to or subsequent to step 113, the control unit 8 can analyse the ECG signal to assess whether it contains an ECG signal for two subjects (i.e. the first subject 16 and the second subject 18), and thus whether the device 2 is being used correctly by the second subject 18. In particular, as the heart rate of the first subject 16 is not likely to be exactly the same to that of the second subject 18, the control unit 8 can analyse the ECG signal to determine whether the ECG signal contains ECG signal components with different heart rates. In some embodiments, the control unit 8 can analyse the ECG signal in the frequency domain to identify the different heart rates. A frequency spectrum (e.g. a fast Fourier transform, FFT, spectrum) of the ECG signal will have a peak corresponding to the heart rate represented by any ECG signal component in the ECG signal, so the control unit 8 can determine the FFT of the ECG signal and identify peaks in the FFT spectrum in a frequency band in which typical heart rates fall (e.g. 30-140 bpm, although other bands can be used in practice). Thus, there will only be one peak (corresponding to one heart rate) if the device 2 is not being used correctly and the heart of the first subject 16 is not in the conductive loop 20, but there will be two peaks if the device 2 is being used correctly. Other techniques for analysing the ECG signal to assess whether it contains an ECG signal for two subjects can make use of peak detection, wavelets, and cross-correlation with a physiological characteristic measurement that can also be derived from the ECG signal (e.g. as described above).

If the control unit 8 cannot detect two different heart rates in the measured ECG signal, then it is likely that the heart of the first subject is not part of the conductive loop 20, and the control unit 8 will not be able to determine the physiological characteristic for the first subject 16. If the control unit 8 cannot detect two different heart rates the control unit 8 can provide feedback to the second subject 18 indicating that the device 2 is not being used correctly or that the second subject 18 needs to contact the first subject 16 differently (for example the second subject 18 needs to hold a hand or arm of the first subject 16). This feedback can be provided visually, for example via a user interface (e.g. a display or warning lights) and/or audibly (e.g. via a speaker).

As noted above, the extracted ECG signal component for the first subject is analysed to determine a measurement of a physiological characteristic in step 115. In embodiments where there are no additional physiological sensors 12, 14 in the device 2, the physiological characteristic for the first subject is one that can be derived completely from the ECG signal itself. For example, the physiological characteristic can be heart rate or heart rate variability (both of which can be determined by calculating the time interval between successive R-peaks). However, in preferred embodiments, the physiological characteristic is blood pressure or another characteristic that can be derived from the ECG signal in combination with a measurement of another physiological characteristic.

Although those skilled in the art will be aware of ways in which blood pressure can be derived from an ECG signal and a measurement of pulse arrival time (PAT) obtained using a PPG sensor located peripherally from the subject's heart (e.g. at a finger or on the forehead), brief details are provided below.

Figure 11:
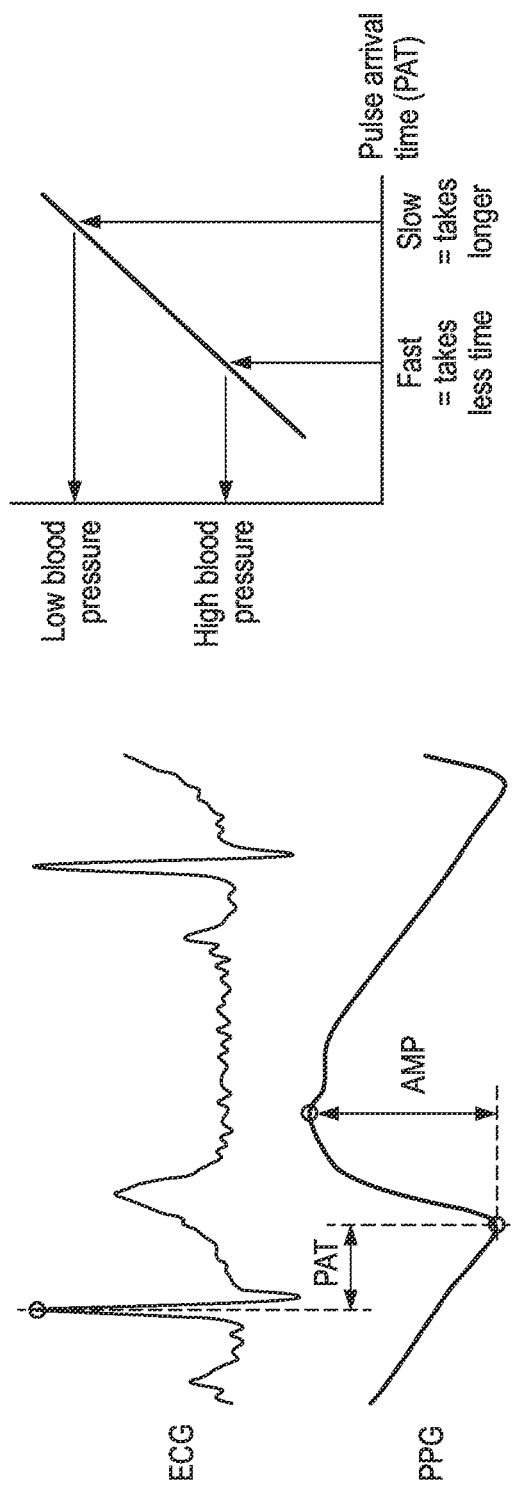
FIG. 11 illustrates an exemplary ECG signal and PPG signal for a subject and a graph that shows the relationship between PAT and blood pressure.

FIG. 11 illustrates an exemplary ECG signal and PPG signal for a single subject over a short period of time (e.g. a few seconds), and a graph that shows the relationship between PAT and blood pressure. One of the R-peaks in the ECG signal is marked, along with the minimum and maximum points on the PPG signal. The PAT can be measured in different ways. In one approach, PAT is given by the time between the R-peak and the foot or minimum of the PPG signal. In another approach, PAT is given by the time between the R-peak to the peak in the PPG signal. The graph of PAT versus blood pressure shows that PAT is inversely proportional to blood pressure, i.e. a decrease in blood pressure leads to an increase in PAT. This relationship between PAT and BP is influenced by age, gender, body height and weight, so a series of calibration functions or tables can be used to determine the blood pressure from a particular PAT measurement.

Figure 12:
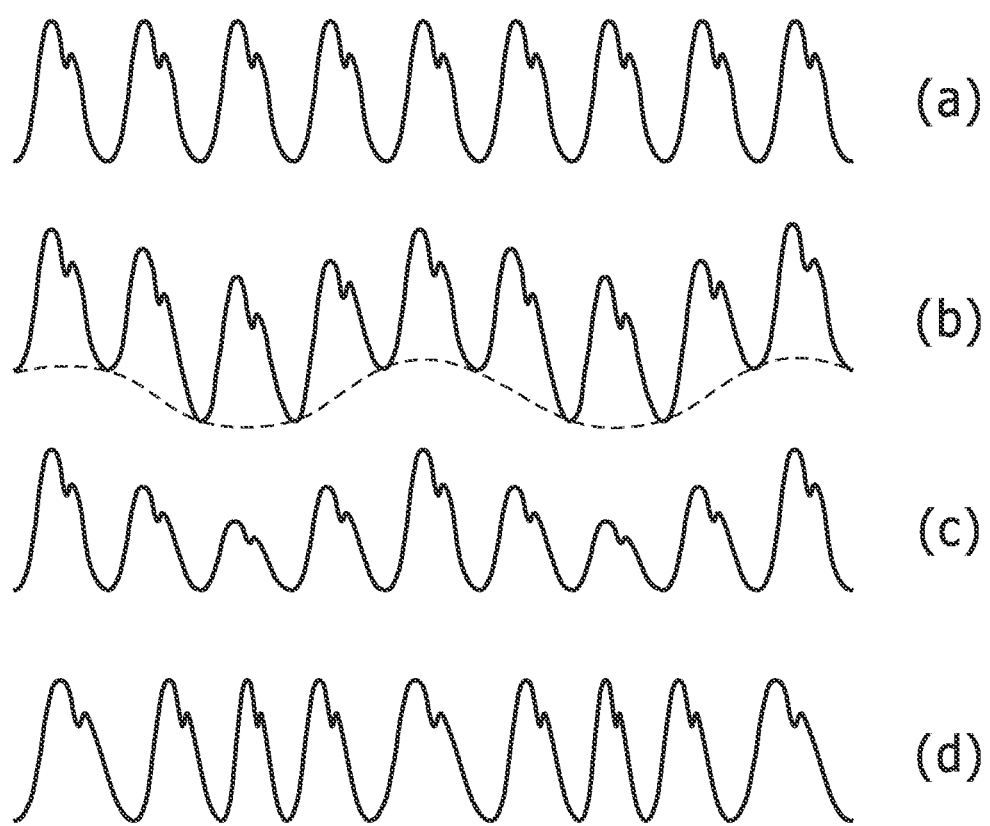
FIG. 12 illustrates examples of an inverted PPG signal covering two complete respiratory cycles with different modulations that indicate heart rate, breathing rate, PPV and HRV.

In embodiments where the device 2 includes a PPG sensor 12 for measuring a PPG signal for the first subject 16, the device 2 can determine additional physiological characteristics for the first subject 16 to the physiological characteristic(s) derived from the ECG signal component for the first subject 16. These additional characteristics include, but are not limited to, heart rate, breathing/respiration rate, heart rate variability (HRV), pulse pressure variability (PPV). FIG. 12 illustrates an inverted PPG signal covering two complete respiratory cycles and indicates how the inverted PPG signal can contain information on the heart rate (the frequency of the peaks/minima in FIG. 12(*a*)), breathing rate (the lower frequency modulation component in FIG. 12(*b*)), pulse pressure variations (the amplitude modulations shown in FIG. 12(*c*)), and heart rate variability (the peak-to-peak interval modulations shown in FIG. 12(*d*)). It will be appreciated that although the different modulations that indicate heart rate, breathing rate, PPV and HRV are shown in different signals in FIG. 12, an actual PPG signal will include each of these modulations simultaneously. Those skilled in the art will be aware of various techniques for determining the heart rate, HRV, respiration/breathing rate and PPV from a PPG signal, and therefore further details are not provided herein.

In some embodiments, in addition to or alternatively to providing an indication of the measured physiological characteristic(s) to the second subject 18 (for example via a display on the device 2 or through a remote device such as a smart phone, tablet or computer), the device 2 can compare the measurements to reference values (e.g. normal values for a healthy individual or a previous measurement for the first subject 16) to determine the amount of deviation. These deviations, or alternatively the measurements of the physiological characteristic(s) themselves can be weighted and combined to provide a 'score' indicating the overall health of the first subject 16.

For example, the device 2 can calculate a 'Basic Health Score' or a 'Full Heath Score' which is similar to the National Early Warning Score of the Royal College of Physicians shown in FIG. 13. In FIG. 13, the non-physiological parameters "any supplemental oxygen" and "level of consciousness" have been struck through because they are not characteristics that can be measured by the described embodiments. However, in an alternative embodiment, values for these two characteristics can be manually entered into the device 2 so they can be used to calculate the health scores. According to the example score system in FIG. 13, the 'Basic Health Score' ranges from 0 to 9 and is based on three parameters: heart rate, respiration rate and PAT-derived BP (which can all be derived according to embodiments of the invention) and the 'Full Health Score' ranges from 0 to 12 (which requires heart rate, respiration rate, PAT-derived BP, oxygen saturation (which can be measured using dual-wavelength PPG) and temperature), which, in the case of both types of score, a higher score indicates a worse health condition for the first subject 16.

It will be appreciated that devices 2 according to the invention can calculate scores using other or further parameters to those mentioned above, such as hemodynamic variability indices (heart rate variability, pulse pressure variability, and PAT variability).

There are therefore provided various embodiments of devices that can be operated by a second subject to obtain a measurement of a physiological characteristic for the first subject from an ECG signal for the first subject.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A device for measuring a physiological characteristic of a first subject, the device comprising:
    a first electrode for contacting a part of the body of the first subject;
    a second electrode for contacting a part of the body of a second subject;
    a control unit for obtaining an electrocardiogram, ECG, signal using the electrodes and for processing the ECG signal to determine a measurement of a physiological characteristic of the first subject; and
    a sensor for measuring a second physiological characteristic of one of the first subject and second subject,
    wherein the signal comprises a first ECG signal component relating to the first subject and a second ECG signal component relating to the second subject, and wherein the control unit is configured to:
        use the measurement of the second physiological characteristic to extract the first ECG signal component relating to the first subject from the ECG signal, and
        process the first ECG signal component to determine a measurement of the physiological characteristic of the first subject.

2. A device as claimed in claim 1, wherein the first ECG signal component comprises R-peaks relating to the first subject and the second ECG signal component comprises R-peaks relating to the second subject, and wherein the control unit is configured to process the ECG signal to identify at least a first set of R-peaks corresponding to one of the first subject and second subject.

3. A device as claimed in claim 2, wherein the control unit is configured to identify the first set of R-peaks as one of (i) the maxima or maxima above a threshold value in the ECG signal; and (ii) the minima or minima below a threshold value in the ECG signal.

4. A device as claimed in claim 1, wherein the second physiological characteristic is a physiological characteristic that can also be derived from the ECG signal.

5. A device as claimed in claim 1, wherein the control unit is configured to use the measurement of the second physiological characteristic to extract the first ECG signal component relating to the first subject by:
    deriving a value for the second physiological characteristic for one or both of the first subject and second subject from the ECG signal;
    comparing the value or values for the second physiological characteristic derived from the ECG signal to the measurement of the second physiological characteristic for said one of the first subject and second subject from the sensor; and
    identifying the ECG signal component in the ECG signal that has a value for the second physiological characteristic closest to the measurement from the sensor as that corresponding to said one of the first subject and second subject.

6. A device as claimed in claim 1, wherein the control unit is configured to use the measurement of the second physiological characteristic to extract the first ECG signal component relating to the first subject by:
    correlating the value or values for the second physiological characteristic with the ECG signal; and
    using the result of the correlation to identify an ECG signal component in the ECG signal corresponding to one of the first subject and second subject.

7. A device as claimed in claim 1, wherein the sensor is for measuring a photoplethysmography, PPG, signal of the one of the first subject and second subject, and the control unit is configured to extract the first ECG signal component as the R-peaks in the ECG signal that correspond to peaks in the PPG signal.

8. A device as claimed in claim 1, wherein the control unit is configured to analyze the ECG signal to determine if it contains ECG signal components for the first subject and the second subject, and to provide feedback to the second subject if the ECG signal contains an ECG signal component for just one subject.

9. A device as claimed in claim 8, wherein the control unit is configured to analyze the ECG signal to determine if it contains ECG signal components for the first subject and the second subject by determining if the ECG signal contains two sets of R-peaks that have opposite polarities to each other.

10. A device as claimed in claim 8, wherein the control unit is configured to analyze the ECG signal to determine if it contains ECG signal components for the first subject and the second subject by analyzing the frequency spectrum of the ECG signal to identify if the ECG signal contains ECG signal components with different heart rates.

11. A method of operating a device to measure a physiological characteristic of a first subject, the method comprising:
receiving an electrocardiogram, ECG, signal using a first electrode that is in contact with a part of the body of the first subject and a second electrode that is in contact with a part of the body of a second subject, wherein the ECG signal comprises a first ECG signal component relating to the first subject and a second ECG signal component relating to the second subject;
receiving a second physiological characteristic of one of the first subject and the second subject from a sensor;
processing the ECG signal to extract the first ECG signal component relating to the first subject by using the measurement of second physiological characteristic; and
processing the first ECG signal component to determine the physiological characteristic of the first subject.

12. A non-transitory computer program product comprising a computer readable medium having computer readable code embodied therein, the computer readable code being configured such that, on execution by a suitable computer, processor or control unit, the computer, processor or control unit is caused to perform the method of claim 11.

13. The method of claim 11, wherein the first ECG signal component comprises R-peaks relating to the first subject and the second ECG signal component comprises R-peaks relating to the second subject, and wherein the method further comprises processing the ECG signal to identify at least a first set of R-peaks corresponding to one of the first subject and second subject.

14. The method of claim 13, wherein the method further comprises identifying the first set of R-peaks as one of (i) the maxima or maxima above a threshold value in the ECG signal; and (ii) the minima or minima below a threshold value in the ECG signal.

15. The method of claim 11, wherein the second physiological characteristic is a physiological characteristic that can also be derived from the ECG signal.

16. The method of claim 11, wherein processing the ECG signal to extract the first ECG signal component relating to the first subject by using the measurement of second physiological characteristic comprises:
deriving a value for the second physiological characteristic for one or both of the first subject and second subject from the ECG signal;
comparing the value or values for the second physiological characteristic derived from the ECG signal to the measurement of the second physiological characteristic for said one of the first subject and second subject from the sensor; and
identifying the ECG signal component in the ECG signal that has a value for the second physiological characteristic closest to the measurement from the sensor as that corresponding to said one of the first subject and second subject.

17. The method of claim 11, wherein processing the ECG signal to extract the first ECG signal component relating to the first subject by using the measurement of second physiological characteristic comprises:
correlating the value or values for the second physiological characteristic with the ECG signal; and
using the result of the correlation to identify an ECG signal component in the ECG signal corresponding to one of the first subject and second subject.

18. The method of claim 11, wherein the sensor is for measuring a photoplethysmography, PPG, signal of the one of the first subject and second subject, and the first ECG signal component is extracted as the R-peaks in the ECG signal that correspond to peaks in the PPG signal.

19. The method of claim 11, wherein the method further comprises analyzing the ECG signal to determine if it contains ECG signal components for the first subject and the second subject, and to provide feedback to the second subject if the ECG signal contains an ECG signal component for just one subject.

20. The method of claim 11, wherein the method further comprises analyzing the ECG signal to determine if it contains ECG signal components for the first subject and the second subject by determining if the ECG signal contains two sets of R-peaks that have opposite polarities to each other.

21. The method of claim 11, wherein the method further comprises analyzing the ECG signal to determine if it contains ECG signal components for the first subject and the second subject by analyzing the frequency spectrum of the ECG signal to identify if the ECG signal contains ECG signal components with different heart rates.

* * * * *